United States Patent [19]

Boëlle et al.

[11] 4,252,826

[45] Feb. 24, 1981

[54] COSMETIC COMPOSITION FOR REMOVING MAKEUP FROM THE EYES

[75] Inventors: Jean-Paul Boëlle; Constantin Koulbanis; Arlette Zabotto nee Arribau, all of Paris, France

[73] Assignee: L'Oreal, Paris, France

[21] Appl. No.: 973,948

[22] Filed: Dec. 28, 1978

[30] Foreign Application Priority Data

Dec. 30, 1977 [FR] France ............................... 77 39840

[51] Int. Cl.³ ............................................. A61K 7/48
[52] U.S. Cl. ............................. 424/361; 424/DIG. 6
[58] Field of Search ............... 424/358, 361, DIG. 6; 536/4

[56] References Cited

U.S. PATENT DOCUMENTS

| | | | |
|---|---|---|---|
| 2,450,079 | 9/1948 | Brown | 536/4 X |
| 2,602,789 | 7/1952 | Schwartz et al. | 536/4 |
| 2,698,819 | 1/1955 | Ziemlak | 424/DIG. 6 |
| 3,435,024 | 3/1969 | Nobile | 536/4 |

FOREIGN PATENT DOCUMENTS

| | | | |
|---|---|---|---|
| 865747 | 8/1945 | France | 424/DIG. 6 |
| 682717 | 2/1965 | Italy | 424/361 |
| 37-4448 | 6/1962 | Japan | 424/361 |
| 240939 | 8/1969 | U.S.S.R. | 424/361 |

OTHER PUBLICATIONS

Sagarin Cosmetics: Science & Technology, 1957, pp. 675, 676, 1034–1039, 1053–1056, 1060–1064, 1067–1070.
Sagarin Cosmetics: Science & Technology, 5/1975, vol. I, pp. 21 and 22.

*Primary Examiner*—Dale R. Ore
*Attorney, Agent, or Firm*—Cushman, Darby & Cushman

[57] ABSTRACT

A cosmetic composition for removing eye makeup includes a mono- or di-alkyl or a mono- or di-alkenyl carboxylate of an α-methyl polyethoxylated glucoside in aqueous solution.

14 Claims, No Drawings

COSMETIC COMPOSITION FOR REMOVING MAKEUP FROM THE EYES

An object of the present invention is to provide a new composition for eye makeup removal which is non-irritating and does not provoke ocular discomfort to the user.

Numerous cosmetic compositions for effecting removal of eye makeup have already been proposed, but they not only irritate the ocular mucous, but also present certain noted inconvenience and discomfort, notably a stinging sensation or ocular discomfort to the user.

In fact, during the operation of removing eye makeup, it is frequently through inadvertence that the composition serving as the makeup remover comes into contact with the ocular mucous and provokes irritation or stinging and tingling sensations, which in certain cases leads to greater complications.

The development of eye makeup removal compositions, which do not provoke irritation or ocular discomfort, presents numerous difficulties because such compositions often contain diverse ingredients which in certain cases can react with each other or can in the long run suffer degradation subsequent to microbial contamination.

After extensive research, a makeup removal lotion for removing eye makeup has been made which comprises a particular class of surface active agents which do not provoke irritation or tingling and stinging sensation of the eye and which are also stable for a lengthy period of time after the first use.

The present invention has for an object a new industrial product, a cosmetic composition for eye makeup removal, which does not irritate or provoke ocular discomfort, which contains an aqueous solution of (i) at least one surface active agent selected from the group consisting of mono- and di-alkyl and mono- and di-alkenyl carboxylates of α-methyl polyethoxylated glucosides and mixtures thereof, said alkyl and alkenyl radicals, being linear or branched, and containing 11 to 21 carbon atoms, and (ii) at least one preservative agent, the pH of said composition being between 4.5 and 8.5, and preferably between 6.5 and 7.5.

According to the invention, the composition for makeup removal from the eyes is preferably in the form of a lotion. The aqueous solution is of demineralized sterilized water, is a flower water (rose water, voilet water, camomile water, and the like) or mixtures thereof.

The mono- and di-alkyl and mono- and di-alkenyl carboxylates of α-methyl polyethoxylated glucosides utilized in the composition of the invention corresponding to formulae A and B below:

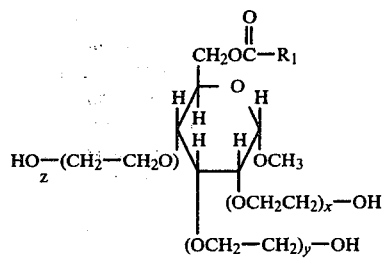

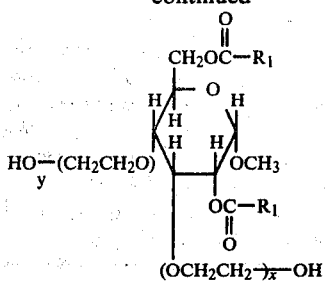

in which: $R_1$ is alkyl or alkenyl, linear or branched, having 11 to 21 carbon atoms, and $x+y(+z)$ represent from 10 to 30 inclusive.

The compounds of this type include the mono- and di-laurates, the mono- and di-palmitates, the mono- and di-stearates, and the mono- and di-oleates of α-methyl polyethoxylated glucoside, which is polyethoxylated with from 10 to 30 moles of ethylene oxide, and mixtures thereof.

According to a preferred embodiment of the invention, a mixture of mono- and di-stearate of α-methyl glucoside ethoxylated with 20 moles of ethylene oxide is used and, in particular, the compound sold by AMERCHOL under the trade denomination of "GLUCAMATE SEE-20" [$R_1=C_{17}H_{35}$ and $x+y(+z)=20$].

In a preferred embodiment, the alkyl carboxylate or alkenyl carboxylate of α-methyl polyethoxylated glucoside is present in the composition in a concentration ranging from about 1 to 5% by weight depending on the extent of lathering power which is desirably conferred to the composition.

According to the invention, a preservative agent is generally contained therein in amounts from 0.002 to 0.3% and preferably from 0.02 to 0.2%.

The preservative agents which can be used in the lotions include: sodium ethyl mercuro thiosalicylate; the digluconate, the diacetate or the dihydrochloride of chlorhexidine; the nitrate of phenylmercury; a mixture containing from 30% of sodium benzoate and 70% of monochloracetamide or a compound corresponding to the formula I:

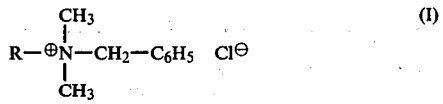

in which: R represents an alkyl of from 12 to 18 carbon atoms or a mixture of said alkyl, as for example, mixtures of $C_{12}$-$C_{14}$ and $C_{14}$-$C_{16}$, and mixtures of said preservative agents.

The compounds of formula (I) above include: the chloride of myristyl-cetyl dimethyl benzylammonium and the, chloride of lauryl-myristyl dimethyl benzylammonium.

According to a particular embodiment of the invention, the compounds of formula (I) are used in association with ethylene diamine tetracetic acid or its dipotassium salt.

In order to maintain the pH of the solutions between 4.5 and 8.5, a mixture of a buffer can be employed and particularly a phosphate buffer (dipotassium hydrogen phosphate/potassium dihydrogen phosphate) or a citrate buffer (sodium citrate/citric acid).

According to a particular embodiment of the invention, the compounds of the invention contain also a humectant such as hexylene glycol, polyethylene glycol 600, etc., these agents permitting a better solubilization of the surface active agent in the aqueous solution.

The eye makeup removal lotion according to the present invention can, in addition, contain other conventional adjuvants such as, for example, softening agents, perfumes, dyes or other surface active agents such as, for example, "Tween 20" (the monolaurate of polyoxyethylenated sorbitan), this latter compound being able to enhance, in certain cases, the solubilization of the prinicapal surface active agent.

It is important, of course, that the adjuvants present are also characterized as not being able to provoke irritation or a stinging and tingling sensation of the ocular mucous.

The softening agents, which can be used, include: allantoin, azulene, and the like.

The following examples illustrate, without limiting, the invention by presenting embodiments of eye makeup removal compositions according to the invention.

EXAMPLES OF COMPOSITIONS

Example A

An eye makeup removal lotion, in accordance with the invention, is prepared from a mixture of the following ingredients:

| | | |
|---|---|---|
| "GLUCAMATE SSE-20", sold by AMERCHOL | 1.5 | g |
| Hexyleneglycol | 1 | g |
| Potassium dihydrogenophosphate | 0.102 | g |
| Dipotassium hydrogen phosphate, 3 H$_2$O | 0.394 | g |
| Chlorhexidine dihydrochloride | 0.08 | g |
| Sodium benzoate | 0.03 | g |
| Monochloracetamide | 0.07 | g |
| Demineralized sterilized water, q.s.p. | 100 | g |

Example B

An eye makeup removal lotion, in accordance with the invention, is prepared by proceeding with a mixture of the following ingredients:

| | | |
|---|---|---|
| "GLUCAMATE SSE-20" | 2 | g |
| Potassium dihydrogenophosphate | 0.102 | g |
| Dipotassium hydrogen phosphate, 3 H$_2$O | 0.394 | g |
| Allantoin | 0.05 | g |
| Lauryl-myristyl dimethyl benzylammonium chloride | 0.0288 | g |
| Dipotassium salt of ethylene diamine tetracetic acid | 0.0104 | g |
| Demineralized sterilized water, q.s.p. | 100 | g |

Example C

An eye makeup removal lotion in accordance with the invention is prepared by proceeding with a mixture of the following ingredients:

| | | |
|---|---|---|
| "GLUCAMATE SSE-20" | 1 | g |
| "Tween 20" monolaurate of polyoxyethylenated sorbitan | 1 | g |
| Potassium dihydrogen phosphate | 0.102 | g |
| Dipotassium hydrogen phosphate, 3 H$_2$O | 0.394 | g |
| Allantoin | 0.05 | g |
| Myristyl-cetyl dimethyl benzylammonium chloride | 0.0288 | g |
| Dipotassium salt of ethylene diamine tetracetic acid | 0.104 | g |
| Demineralized sterilized water, q.s.p. | 100 | g |

What is claimed is:

1. A cosmetic composition for removing makeup from the eyes, which is non-irritating and does not provoke ocular difficulty, which comprises an aqueous solution of:
   (i) at least one surface active agent selected from the group consisting of mono-alkyl carboxylate of α-methyl polyethoxylated glucoside, di-alkyl carboxylate of α-methyl polyethoxylated glucoside, mono-alkenyl carboxylate of α-methyl polyethoxylated glucoside, di-alkenyl carboxylate of α-methyl polyethoxylated glucoside which are ethoxylated with 10 to 30 moles of ethylene oxide and a mixture thereof, wherein said alkyl and alkenyl moieties are linear or branched and have 11 to 21 carbon atoms, and
   (ii) at least one preservative agent selected from the group consisting of sodium ethylmercurothiosalicylate, the digluconate of chlorhexidine, the diacetate of chlorhexidine or the dihydrochloride of chlorhexidine, phenylmercuronitrate, a mixture of 30% sodium benzoate and 70% mono-chloracetamide, a compound of formula I

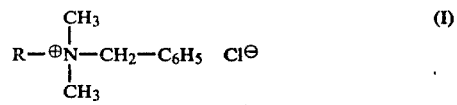

wherein R is akyl having 12 to 18 carbon atoms or a mixture thereof, and a mixture of said preservatives, the pH of said composition being between 4.5 and 8.5.

2. The composition according to claim 1 wherein said surface active agent is selected from the group consisting of α-methyl polyethoxylated glucoside of mono-laurate, di-laurate, α-methyl polyethoxylated glucoside of mono-palmitate, α-methyl polyethoxylated glucoside of di-palmitate, α-methyl polyethoxylated glucoside of mono-stearate, α-methyl polyethoxylated glucoside of di-stearate, α-methyl polyethoxylated glucoside of mono-oleate, α-methyl polyethoxylated glucoside of di-oleate, and a mixture thereof, polyethoxylated with 10 to 30 moles of ethylene oxide, and a mixture thereof.

3. The composition of claim 1, wherein the surface active agent is a mixture of a α-methyl glucoside mono-stearate and of a α-methyl glucoside di-stearate ethoxylated with 20 moles of ethylene oxide.

4. The composition according to claim 1 wherein the surface active agent is present in an amount of from 1 to 5%.

5. The composition of claim 1, wherein the preservative is a compound of formula I wherein R is a mixture of alkyls containing 12 to 14 carbon atoms or a mixture of alkyls containing 14 to 16 carbon atoms.

6. The composition according to claim 1, characterized by the fact that the compound of formula I is the chloride of myristyl-cetyl dimethylbenzylammonium or the chloride of lauryl-myristyl dimethylbenzylammonium.

7. The composition according to claim 1, characterized by the fact that the compound of formula I associated with ethylene diamine tetracetic acid or dipotassium salt of ethylenediamine tetracetic acid.

8. The composition according to claim 1, wherein the preservative agent is present in a proportion between 0.002 and 0.3%.

9. The composition of claim 8, wherein the preservative is present in an amount of from 0.02 to 0.2%.

10. The composition according to claim 1, which contains a phosphate buffer or a citrate buffer.

11. The composition according to claim 1, wherein the pH is between 6.5 and 7.5.

12. The composition according to claim 1, which contains a humectant selected from the group consisting of hexylene glycol and polyethyleneglycol 600.

13. The composition of claim 1 which also includes at least one adjuvant selected from the group consisting of a softening agent, a perfume, a colorant, a dye, and another surface active agent.

14. A cosmetic composition for removing eye makeup, which is non-irritating and does not provoke ocular difficulty, comprising an aqueous solution of, as a surface active agent, a mixture of mono-stearate $\alpha$-methyl glucoside ethoxylated with 20 moles of ethylene oxide and di-stearate of $\alpha$-methyl glucoside ethoxylated with 20 moles of ethylene oxide, said surface active agent being present in an amount of about 1 to 5 percent by weight of said composition and from 0.002 to 0.3 percent by weight of a preservative selected from the group consisting of chlorhexidine dihydrochloride, lauryl-myristyl dimethyl benzylammonium chloride and myristyl-cetyl dimethyl benzylammonium chloride, said composition having a pH between 4.5 and 8.5.

* * * * *